US009064153B2

(12) United States Patent
Lin et al.

(10) Patent No.: US 9,064,153 B2
(45) Date of Patent: Jun. 23, 2015

(54) VIDEO DEVICE FOR REALTIME PEDALING FREQUENCY ESTIMATION

(71) Applicant: National Chung Cheng University, Chia-Yi (TW)

(72) Inventors: Tay-Jyi Lin, Chiayi County (TW); Ching-Wei Yeh, Chia-Yi (TW); Yuan-Hsiang Miao, Taichung (TW); Shau-Chian Tang, Taipei (TW)

(73) Assignee: National Chung Cheng University, Chia-Yi (TW)

( * ) Notice: Subject to any disclaimer, the term of this patent is extended or adjusted under 35 U.S.C. 154(b) by 0 days.

(21) Appl. No.: 14/255,604

(22) Filed: Apr. 17, 2014

(65) Prior Publication Data

US 2015/0146918 A1    May 28, 2015

(30) Foreign Application Priority Data

Nov. 26, 2013 (TW) .............................. 102142985 A

(51) Int. Cl.
| | | |
|---|---|---|
| *G06K 9/00* | (2006.01) | |
| *G01P 3/36* | (2006.01) | |
| *G06T 7/20* | (2006.01) | |
| *H04N 7/18* | (2006.01) | |
| *G01P 15/00* | (2006.01) | |

(52) U.S. Cl.
CPC .............. *G06K 9/00711* (2013.01); *G01P 3/36* (2013.01); *G06T 7/20* (2013.01); *H04N 7/18* (2013.01); *G06K 9/00791* (2013.01)

(58) Field of Classification Search
USPC ........... 382/10, 103, 106–107, 122, 162, 168, 382/173, 181, 189, 199, 209, 219, 232, 254, 382/274, 276, 288–294, 305, 312; 73/504.8, 488, 493; 482/3, 57; 701/37
See application file for complete search history.

(56) References Cited

U.S. PATENT DOCUMENTS

| | | | | |
|---|---|---|---|---|
| 4,526,036 | A | * | 7/1985 | Morrison ........................ 73/493 |
| 6,199,021 | B1 | | 3/2001 | Cote et al. |
| 6,356,848 | B1 | | 3/2002 | Cote et al. |
| 2005/0282685 | A1 | * | 12/2005 | Panatta ............................ 482/3 |
| 2009/0011907 | A1 | * | 1/2009 | Radow et al. ................... 482/57 |
| 2011/0202236 | A1 | * | 8/2011 | Galasso et al. ................. 701/37 |
| 2012/0042725 | A1 | * | 2/2012 | Cote et al. ....................... 73/488 |
| 2014/0305204 | A1 | * | 10/2014 | Hong et al. ................. 73/504.08 |

* cited by examiner

*Primary Examiner* — Seyed Azarian
(74) *Attorney, Agent, or Firm* — Muncy, Geissler, Olds & Lowe, P.C.

(57) ABSTRACT

A video device for realtime pedaling frequency estimation is mounted on a bike and comprises an image capture unit capturing continuous dynamic images of an upper body of a biker; an image recognition unit recognizing images of symmetric regions of the biker and images of swings of the symmetric regions from the continuous dynamic images; a microprocessor calculating a frequency of periodical swings of the biker from the images of the symmetric regions and the images of the swings of the symmetric regions, and then obtaining a pedaling frequency; and a display device presenting the pedaling frequency, wherein a widely-used intelligent handheld device replaces the sensors, display device, and complicated circuits of the conventional cyclometer, and wherein a novel image recognition technology is used to measure the pedaling frequency with a considerable accuracy in a lower cost and a convenient way.

9 Claims, 4 Drawing Sheets

VIDEO DEVICE FOR REALTIME PEDALING FREQUENCY ESTIMATION

This application claims priority for Taiwan patent application no. 102142985 filed at Nov. 26, 2013, the content of which is incorporated by reference in its entirely.

BACKGROUND OF THE INVENTION

1. Field of the Invention

The present invention relates to a video device, particularly to a video device for realtime pedaling frequency estimation.

2. Description of the Related Art

Nowadays, more and more people like to enjoy leisure activities. Among various outdoor leisure activities, biking is a sport very suitable to modern people, not only refreshing people in natural environments but also exercising their bodies. Many biking fans have established their teams for enjoying biking races or mountain biking.

While enjoying biking tours, bikers may have interest in some biking parameters, such as speed, distance, gear ratio, smoothness, balance, etc. The speed and distance of biking correlate with the physical performance and energy consumption of the biker. The conventional technology uses GPS (Global Positioning System) to track the path of biking, and uses the length of the path and the time of biking to calculate the speed. As long as the device can link to the Internet wirelessly, the conventional technology can estimate the speed of biking. However, the speed obtained by the conventional technology is unlikely to evaluate the physical performance and energy consumption of the biker because it does not take the factor of landforms into consideration. In fact, the pedaling frequency is more likely to indicate the physical performance and energy consumption of the biker.

The current bike cyclometers have been widely used to measure the biking speed and pedaling frequency. The improvement in the sampling technology has made the measurement of biking parameters more and more accurate. For an example, n pieces of magnets are annularly arranged in the gear disc or the crank of a bike, and the sensor detects the pass of n pieces of magnets each cycle of rotations of the gear disc, whereby the processing unit can work out the pedaling force and power output of the biker and the speed variation of the bike. For another example, a chain speed sensor and a chain tension sensor are respectively used to detect the speed and tension of the chain. As the chain is driven by the pedals, the frequency of chain rotation is identical to the frequency of pedal rotation. Therefore, the conventional technology can really detect the pedaling frequency.

In order to measure the pedaling frequency of the biker in an electric or magnetic induction way, sensors and magnets must be installed in a bike. Thus, the pedal mechanism, including the central shaft and the gear disc, must be greatly modified or replaced with dedicated components. Further, a complicated circuit must be installed to connect the hardware components with the sensors and the display device. Furthermore, the sensor installed in the fork rake must be very close to the magnets installed in the crank so as to undertake measurement accurately. Therefore, the installation is troublesome and complicated in the conventional technologies. Moreover, different brands of bikes need different pedal mechanisms and different wirings. Thus, the hardware cost is pretty high for detecting biking parameters in the conventional technologies. The abovementioned problems have impaired the application of the conventional bike cyclometers.

Accordingly, the present invention proposes a video device for realtime pedaling frequency estimation to overcome the abovementioned problems.

SUMMARY OF THE INVENTION

The primary Objective of the present invention is to provide a video device for realtime pedaling frequency estimation, wherein an intelligent handheld device, which has been easily available for people now, is mounted on a bike, and wherein the existing camera of the handheld device captures the continuous dynamic images of the periodical swings of the biker, whereby the present invention can calculate and display the pedaling frequency in realtime, neither using any extra hardware device, such as the sensor, screen or wireless transceiver, nor needing complicated circuitry, wherefore the present invention obviously decreases the cost of design and fabrication and effectively reduces thefts of the bike device.

Another objective of the present invention is to provide a video device for realtime pedaling frequency estimation, which is easy to mount and dismount, and which uses the existing intelligent handheld devices that are widely used in modern living to obtain the information of pedal frequencies accurately in realtime, wherefore the present invention can replace the expensive conventional cyclometers and exempt the manufactures from the troublesome and complicated procedures of installing the conventional cyclometers.

To achieve the abovementioned objectives, the present invention proposes a video device for realtime pedaling frequency estimation, which comprises an image capture unit, an image recognition unit, a microprocessor, and a display device. The image capture unit captures the continuous dynamic images of the upper body of a biker. The image recognition unit is electrically connected with the image capture unit and automatically recognizes the images of the symmetric regions of the biker and the images of the relative swings of the symmetric regions. The microprocessor is electrically connected with the image recognition and the display device, uses the images of the symmetric regions and the images of the relative swings of the symmetric regions to work out the frequency of the periodical swings of the biker, and thus obtains the pedaling frequency of the biker, which is identical to the frequency of the periodical swings of the biker. Then, the display device presents information of the pedaling frequency.

Below, the embodiments are described in detail to make easily understood the objectives, technical contents, characteristics and accomplishments of the present invention.

DETAILED DESCRIPTION OF THE INVENTION

The intelligent handheld devices, such as smartphones and tablet computers, have been popularized globally. In fact, almost everyone has his own intelligent handheld device. Besides, the application of multimedia is also being diversified. Considering cost and convenience, the present invention proposes a video device for realtime pedaling frequency estimation, wherein a smartphone is mounted on a bike, and the existing functions of the smartphone are used to measure the pedaling frequency of the biker. Thereby, the present invention uses the least hardware device to measure the pedaling frequency without varying the original structure of the bike. The video device of the present invention is not only easy to mount and dismount but also able to replace the conventional complicated and expensive cyclometers. It is expected that the present invention should bring much convenience to people and have high commercial potential.

Figure 1:
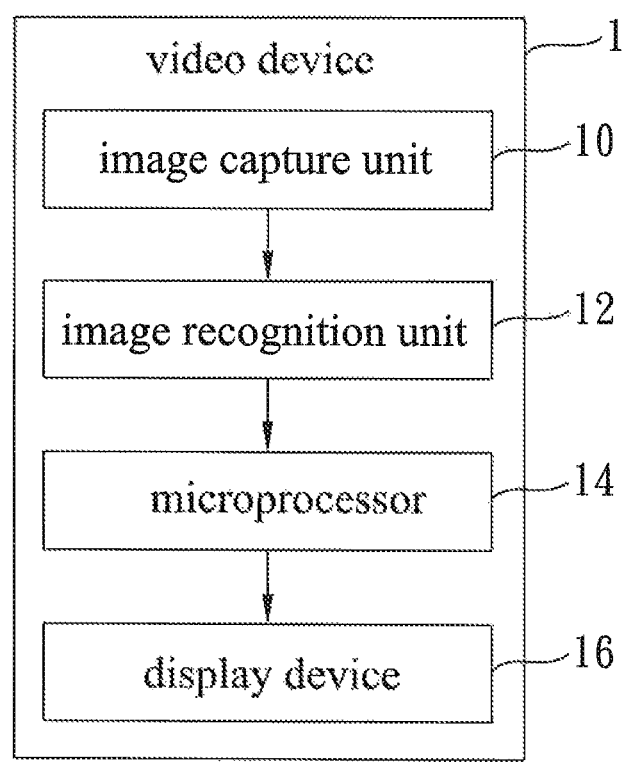
FIG. 1 is a block diagram schematically showing the system of a video device for realtime pedaling frequency estimation according to one embodiment of the present invention.
Figure 2:
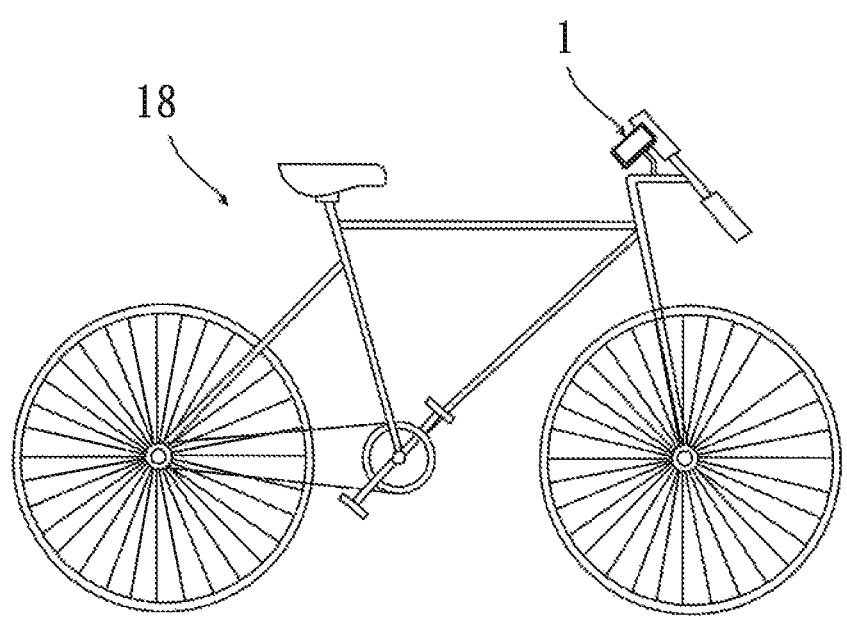
FIG. 2 is a diagram schematically showing a video device for realtime pedaling frequency estimation mounted on a bike according to one embodiment of the present invention.

Refer to FIG. 1 and FIG. 2. FIG. 1 is a block diagram schematically showing the system of a video device for realtime pedaling frequency estimation according to one embodiment of the present invention. FIG. 2 is a diagram schematically showing a video device for realtime pedaling frequency estimation mounted on a bike according to one embodiment of the present invention. The video device 1 for realtime pedaling frequency estimation of the present invention comprises an image capture unit 10, an image recognition unit 12, a microprocessor 14, and a display device 16. The image recognition unit 12 is electrically connected with the image capture unit 10. The microprocessor 14 is electrically connected with the image recognition unit 12 and the display device 16. The image capture unit 10 is CCD (Charge Coupled Device) or a CMOS (Complementary Metal Oxide Semiconductor) sensor. Before operation, the video device 1 is mounted at the front of a bike 18, i.e. at the position between two handlebars. While the biker rides the bike 18, the image capture unit 10 captures the continuous dynamic images of the upper body of the biker. While the biker pushes the left pedal and the right pedal alternately to drive the chain, his body swings leftward and rightward alternately. The image recognition unit 12 automatically recognizes the images of the symmetric regions of the biker, such as two shoulders or two ears of the biker, and the images of the swings of the symmetric regions from the continuous dynamic images. The microprocessor 14 uses the images of the symmetric regions and the images of the swings of the symmetric regions to work out the frequency of the periodical swings of the biker, and thus obtains the pedaling frequency of the biker, which is identical to the frequency of the periodical swings of the biker. Then, the display device 16 presents information of the pedaling frequency.

Figure 3A:
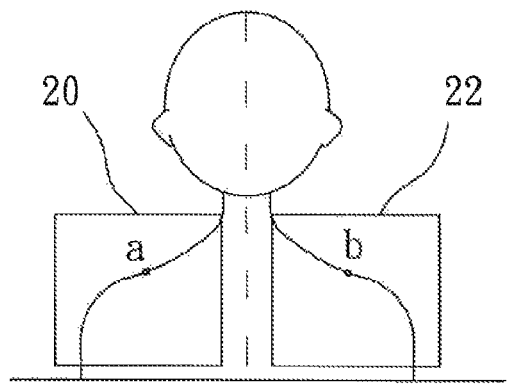
FIGS. 3A-3C are diagrams schematically showing the symmetric regions and the relative swing thereof according to one embodiment of the present invention.

The present invention adopts the symmetric regions of the upper body as ROI (Regions Of interest). The image recognition unit 12 automatically recognizes the symmetric regions, which undertake relative swings, from the continuous dynamic images. Refer to FIG. 3A, wherein the left shoulder image 20 and the right shoulder image 22 are used to exemplify the images of the symmetric regions. The image recognition unit 12 is a human image recognition program built in the microprocessor 14. After having recognized the left shoulder image 20 and the right shoulder image 22 symmetric to each other from the continuous dynamic images, the image recognition unit 12 establishes a first reference point a and a second reference point b respectively at the left shoulder image 20 and the right shoulder image 22. Then, the image recognition unit 12 continuously captures the variation of the tilt angles of the first reference point a and the second reference point b as the images of the relative swings of the symmetric regions. The details thereof are described below. The image recognition unit 12 uses an edge detection method to detect the edge pixels having dramatic gradient variation in the continuous dynamic images. The edge detection methods include methods using Canny operators, Sobel operators, Prewitt operators, Robert operators, or Laplacian operators. In one embodiment, the Canny operator is used to process the result of the edge detection. Then, the Hough Transform uses several straight lines or curved lines to connect the edge pixels and eliminates unwanted noise signals to define a left shoulder line of the left shoulder image 20 and a right shoulder line of the right shoulder image 22. In order to calculate the tilt angles of the left shoulder line and the right shoulder line, the intersection point of the neck of the biker and the left shoulder line is used as the start point of the left shoulder line, and intersection point of the neck of the biker and the right shoulder line is used as the start point of the right shoulder line. The first reference point a is a point at the left shoulder line and separated from the start point of the left should line by 50 pixels, which is about the middle point of the left shoulder line. The second reference point b is a point at the right shoulder line and separated from the start point of the right should line by 50 pixels, which is about the middle point of the right shoulder line. The microprocessor 14 uses the period of the swings of the left shoulder line and the right shoulder line and the variation of the relative tilt angle to calculate the frequency of the periodical swings of the biker, and thus obtains the pedaling frequency of the biker, which is identical to the frequency of the periodical swings of the biker.

Figure 3B:
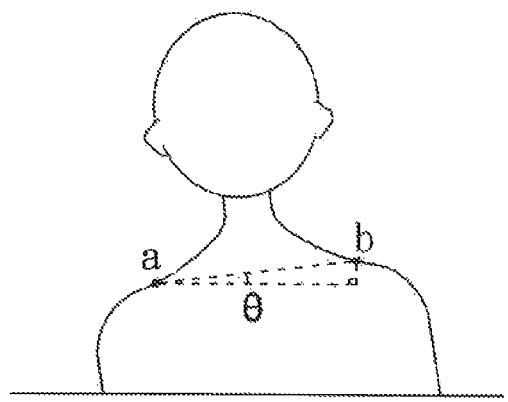
Figure 3C:
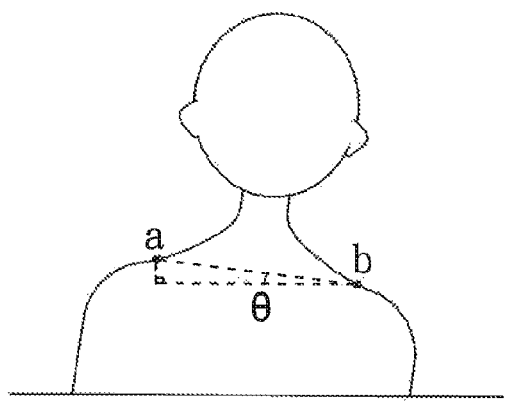
Figure 4:
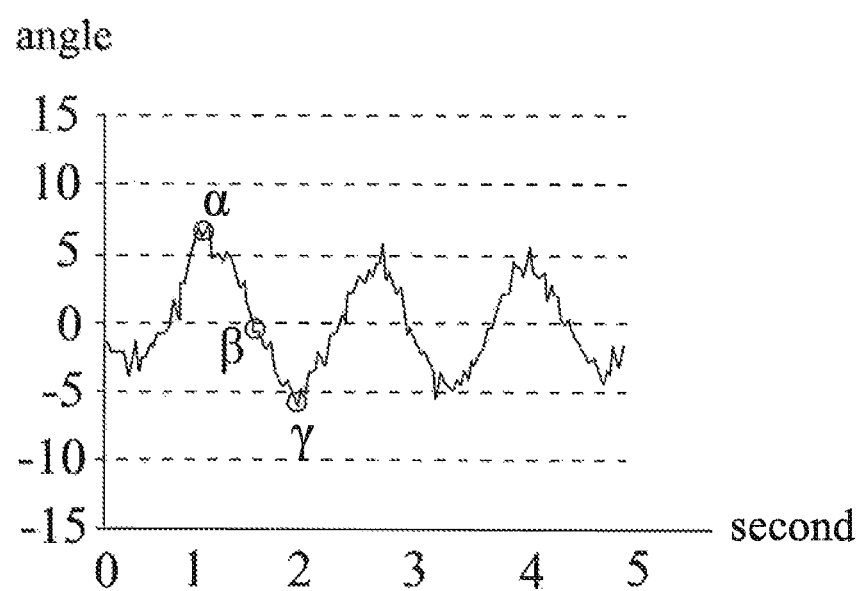
FIG. 4 shows a waveform of the period of the swings of the biker according to one embodiment of the present invention.

Refer to FIG. 3B, FIG. 3C and FIG. 4. FIG. 4 shows a waveform of the periods of the swings of the biker according to one embodiment of the present invention, wherein Point α is the tilt angle of the first reference point of the left shoulder line of the biker; Point γ is the tilt angle of the second reference point of the right shoulder line of the biker; Point β is the intersection of the first reference point a and the second reference point b. As shown in FIG. 3B, while the left foot of the biker pushes down the pedal, the first reference point a of the left shoulder line descends by a tilt angle θ with respect to the second reference point b of the right shoulder line. As shown in FIG. 3C, while the right foot of the biker pushes down the pedal, the second reference point b of the right shoulder line descends by a tilt angle θ with respect to the first reference point a of the left shoulder line. As shown in FIG. 4, the tilt angle at Point α is 6 degrees; the tilt angle at point β is zero degree; the tilt angle at point γ is −6 degrees. Via tracking the tilt angle varying during the swings of the shoulder lines, the time interval between Point α—the maximum and Point γ—the minimum, i.e. the period of the swings, is learned. Thus, the pedaling frequency is also learned.

In some embodiments, the left ear and the right ear are used as the symmetric regions to measure the pedaling frequency. A first reference point and a second reference point are respectively established on a left ear image and a right ear image. The images of continuous variation of the tilt angles of the first reference point a and the second reference point b are used as the swing images. The image recognition unit 12 uses an edge detection method to detect the edge pixels having dramatic gradient variation in the continuous dynamic images and uses the Hough Transform to connect the edge pixels to define a left ear contour line and a right ear contour line. The microprocessor 14 uses the period of the swings of the left ear contour line and the right ear contour line and the variation of the relative tilt angle to calculate the pedaling frequency of the biker. Thereby, the present invention can detect and track the frequency of the periodical swings of two shoulders or two ears of the biker, merely using the image processing technology. As the frequency of the periodical swings of the biker is consistent with the pedaling frequency of the biker, the present can obtain the pedaling frequency accurately. Further, the microprocessor 14 can also use the pedaling frequency, the gear ratio and the wheel diameter of the bike to work out the speed of the bike. As different brands of bikes have more or less difference in structure, the parameters of the gear ratio and wheel diameter should be input to the video device before speed estimation. Then, the video device can use the parameters and the image processing technology to accurately estimate the speed of the bike. The present invention applies to various brands and various types of bikes without changing the original structures of the bikes. Therefore, the present invention has high flexibility in application and has high potential in the market.

In conclusion, the present invention proposes a novel technology for measuring the pedaling frequency of the biker, which mounts an intelligent handheld device, which is easily available for the biker, on a bike and uses the existing camera (the image capture unit) to capture the continuous dynamic images of periodical swings of the biker, and which uses the microprocessor and the human image recognition program (the image recognition unit) to estimate and display the pedaling frequency of the biker in realtime. The microprocessor of the intelligent handheld device has been evolved from the single core CPU to the octa core CPU. The octa core CPU uses 8 pieces of microprocessors to process all the application programs (such as APPS) and thus can fast and accurately estimate the pedaling frequency. Then, the display unit presents information to the biker in realtime. The present invention neither needs any extra hardware device, such as the sensor, screen or wireless transceiver, nor uses any complicated circuitry. Hence, the present invention can obviously reduce the cost of design and fabrication. Further, the present invention is easy to mount and dismount. Thus, the present invention is exempted from the troublesome and complicated assembly procedures of the conventional cyclometer and less likely to be stolen. Therefore, the present invention would bring much convenience to people and have high commercial potential.

The embodiments described above are only to exemplify the present invention but not to limit the scope of the present invention. Any equivalent modification or variation according to the characteristic or spirit of the present invention is to be also included within the scope of the present invention.

What is claimed is:

1. A video device for realtime pedaling frequency estimation, mounted on a bike and comprising:
   an image capture unit capturing continuous dynamic images of an upper body of a biker;
   an image recognition unit electrically connected with said image capture unit and recognizing images of symmetric regions of said biker and images of swings of said symmetric regions from said continuous dynamic images;
   a microprocessor electrically connected with said image recognition unit, calculating a frequency of periodical swings of said biker from said images of said symmetric regions and said images of said swings of said symmetric regions, and then obtaining a pedaling frequency; and
   a display device electrically connected with said microprocessor and presenting information of said pedaling frequency;
   wherein said images of said symmetric regions are a left shoulder image and a right shoulder image of said biker, and wherein a first reference point and a second reference point are respectively established at said left shoulder image and said right shoulder image of said biker, and wherein images of continuous variation of a relative tilt angle of said first reference point and said second reference point are used as said images of said swings of said symmetric regions; and
   wherein said image recognition unit uses an edge detection method to detect edge pixels having dramatic gradient variation in said continuous dynamic images and uses a Hough Transform to connect said edge pixels to define a left shoulder line of said left shoulder image and a right shoulder line of said right shoulder image.

2. The video device for realtime pedaling frequency estimation according to claim 1, wherein said microprocessor uses said pedaling frequency, a gear ratio of said bike, and a wheel diameter of said bike to work out speed of said bike.

3. The video device for realtime pedaling frequency estimation according to claim 1, wherein said microprocessor uses a period of swings of said left shoulder line and said right shoulder line and variation of a relative tilt angle of said left shoulder line and said right shoulder line to calculate said frequency of said periodical swings of said biker, and then obtains said pedaling frequency.

4. The video device for realtime pedaling frequency estimation according to claim 1, wherein an intersection of said left shoulder line and a neck of said biker is used as a start point of said left shoulder line, and said first reference point is defined via extending said start point of said left shoulder line outward by 50 pixels, and wherein an intersection of said right shoulder line and said neck of said biker and is used as a start point of said right shoulder line, and said second reference point is defined via extending said start point of said right shoulder line outward by 50 pixels.

5. The video device for realtime pedaling frequency estimation according to claim 1, wherein said images of said symmetric regions are a left ear image and a right ear image of said biker, and wherein a first reference point and a second reference point are respectively established at said left ear image and said right ear image of said biker, and wherein images of continuous variation of a relative tilt angle of said first reference point and said second reference point are used as said images of said swings of said symmetric regions.

6. The video device for realtime pedaling frequency estimation according to claim 5, wherein said image recognition unit uses an edge detection method to detect edge pixels having dramatic gradient variation in said continuous dynamic images and uses a Hough Transform to connect said edge pixels to define a left ear contour line of said left ear image and a right ear contour line of said right ear image.

7. The video device for realtime pedaling frequency estimation according to claim 5, wherein said microprocessor uses a period of swings of said left ear contour line and said right ear contour line and variation of a relative tilt angle of said left ear contour line and said right ear contour line to calculate said frequency of said periodical swings of said biker, and then obtains said pedaling frequency.

8. The video device for realtime pedaling frequency estimation according to claim 1, wherein said image capture unit is CCD (Charge Coupled Device) or a CMOS (Complementary Metal Oxide Semiconductor) sensor.

9. The video device for realtime pedaling frequency estimation according to claim 1, wherein said image recognition unit is a human image recognition program built in said microprocessor.

* * * * *